(12) United States Patent
Lee et al.

(10) Patent No.: US 11,497,423 B2
(45) Date of Patent: *Nov. 15, 2022

(54) SYSTEM AND METHOD FOR DETECTING PHYSIOLOGICAL STATE

(71) Applicant: NURALOGIX CORPORATION, Toronto (CA)

(72) Inventors: Kang Lee, Toronto (CA); Pu Zheng, Toronto (CA)

(73) Assignee: NURALOGIX CORPORATION, Toronto (CA)

( * ) Notice: Subject to any disclaimer, the term of this patent is extended or adjusted under 35 U.S.C. 154(b) by 295 days.

This patent is subject to a terminal disclaimer.

(21) Appl. No.: 16/948,886

(22) Filed: Oct. 5, 2020

(65) Prior Publication Data
US 2021/0068735 A1  Mar. 11, 2021

Related U.S. Application Data

(63) Continuation of application No. 16/875,339, filed on May 15, 2020, now Pat. No. 10,806,390, which is a
(Continued)

(51) Int. Cl.
*G06K 9/00* (2022.01)
*A61B 5/16* (2006.01)
(Continued)

(52) U.S. Cl.
CPC ............ *A61B 5/165* (2013.01); *A61B 5/0035* (2013.01); *A61B 5/0077* (2013.01); *A61B 5/024* (2013.01);
(Continued)

(58) Field of Classification Search
CPC ..... A61B 5/165; A61B 5/0035; A61B 5/0077; A61B 5/024; A61B 5/02438;
(Continued)

(56) References Cited

U.S. PATENT DOCUMENTS 6,102,846 A * 8/2000 Patton .................... G16H 30/40
600/26
6,126,595 A 10/2000 Amano et al.
(Continued)

FOREIGN PATENT DOCUMENTS

CA  2725599 A1 * 12/2009  ........... C12Q 1/6883
CA  2942852 A1   9/2014
(Continued)

OTHER PUBLICATIONS

Ramirez et al., "Color Analysis of Facial Skin: Detection of Emotional State", 2014, pp. 468-473.
(Continued)

*Primary Examiner* — Mahendra R Patel
(74) *Attorney, Agent, or Firm* — Bhole IP Law; Anil Bhole; Marc Lampert

(57) ABSTRACT

A system and method for health diagnostics and more specifically to an image-capture based system and method for detecting physiological state for a subject. The system provides a remote and non-invasive approach by which to detect physiological state with a high confidence. The system enables monitoring of hemoglobin concentration changes by optical imaging and related detection systems.

16 Claims, 12 Drawing Sheets

Related U.S. Application Data continuation of application No. 16/076,522, filed as application No. PCT/CA2017/050207 on Feb. 17, 2017, now Pat. No. 10,694,988.

(60) Provisional application No. 62/296,163, filed on Feb. 17, 2016.

(51) Int. Cl.

| A61B 5/024 | (2006.01) |
| --- | --- |
| A61B 5/055 | (2006.01) |
| A61B 5/145 | (2006.01) |
| A61B 5/00 | (2006.01) |
| A61B 5/369 | (2021.01) |
| G06N 20/00 | (2019.01) |
| A61B 5/026 | (2006.01) |
| G06N 3/08 | (2006.01) |
| G06T 5/00 | (2006.01) |
| G06T 7/00 | (2017.01) |

(52) U.S. Cl.
CPC .......... *A61B 5/0261* (2013.01); *A61B 5/0263* (2013.01); *A61B 5/02438* (2013.01); *A61B 5/055* (2013.01); *A61B 5/145* (2013.01); *A61B 5/369* (2021.01); *A61B 5/7207* (2013.01); *A61B 5/7257* (2013.01); *G06N 3/08* (2013.01); *G06N 20/00* (2019.01); *G06T 5/003* (2013.01); *G06T 7/0014* (2013.01); *G06T 2207/10016* (2013.01); *G06T 2207/30096* (2013.01)

(58) Field of Classification Search
CPC ..... A61B 5/0261; A61B 5/0263; A61B 5/055; A61B 5/145; A61B 5/369; A61B 5/7207; A61B 5/7257; G06N 3/08; G06N 20/00; G06T 5/003; G06T 7/0014; G06T 2207/10016; G06T 2207/30096
USPC .......................................................... 382/128
See application file for complete search history.

(56) References Cited

U.S. PATENT DOCUMENTS

| 9,693,696 | B2 | 7/2017 | Kovacs et al. | |
| --- | --- | --- | --- | --- |
| 2005/0054935 | A1 | 3/2005 | Rice et al. | |
| 2007/0021678 | A1 | 1/2007 | Beck et al. | |
| 2007/0100666 | A1 | 5/2007 | Stivoric et al. | |
| 2008/0002892 | A1 | 1/2008 | Jelonek et al. | |
| 2008/0294012 | A1* | 11/2008 | Kurtz | A61B 5/444 |
| | | | | 600/300 |
| 2008/0294013 | A1* | 11/2008 | Gobeyn | A61B 5/445 |
| | | | | 600/300 |
| 2009/0310828 | A1 | 12/2009 | Kakadiaris et al. | |
| 2010/0152600 | A1* | 6/2010 | Droitcour | A61B 5/1113 |
| | | | | 600/534 |
| 2011/0004110 | A1* | 1/2011 | Shusterman | G16H 50/20 |
| | | | | 600/509 |
| 2011/0251493 | A1* | 10/2011 | Poh | G06V 10/7715 |
| | | | | 382/128 |
| 2013/0116263 | A1* | 5/2013 | Campbell | A61P 43/00 |
| | | | | 514/264.11 |
| 2014/0128690 | A1 | 5/2014 | Leboeuf | |
| 2014/0313303 | A1* | 10/2014 | Davis | A61B 5/68 |
| | | | | 348/77 |
| 2014/0330089 | A1 | 11/2014 | Webb | |
| 2014/0347265 | A1 | 11/2014 | Aimone et al. | |
| 2014/0364721 | A1* | 12/2014 | Lee | A61B 5/0036 |
| | | | | 600/411 |
| 2014/0378810 | A1* | 12/2014 | Davis | G06F 16/245 |
| | | | | 600/407 |
| 2015/0078642 | A1* | 3/2015 | Fang | G06T 7/0012 |
| | | | | 382/131 |
| 2015/0190061 | A1 | 7/2015 | Godavarty et al. | |
| 2015/0313496 | A1 | 11/2015 | Connor | |
| 2016/0015284 | A1 | 1/2016 | Grudic et al. | |
| 2017/0000356 | A1 | 1/2017 | Smith, Sr. | |

FOREIGN PATENT DOCUMENTS

| CA | 2962083 | A1 | 4/2016 | |
| --- | --- | --- | --- | --- |
| CN | 101394786 | A | 3/2009 | |
| CN | 102973279 | B | 9/2014 | |
| CN | 106999111 | A | 8/2017 | |
| EP | 2762066 | A1 | 8/2014 | |
| EP | 3008686 | A4 | 12/2014 | |
| WO | WO-2008079412 | A2 * | 7/2008 | ......... A01K 67/0271 |
| WO | WO-2009115478 | A2 * | 9/2009 | .......... C12Q 1/6883 |
| WO | WO-2011109398 | A2 * | 9/2011 | ........... A61K 31/198 |
| WO | WO-2012003523 | A1 * | 1/2012 | ............. G10L 17/26 |
| WO | WO-2014043255 | A1 * | 3/2014 | ......... A61B 5/02416 |
| WO | 2015165188 | A1 | 11/2015 | |
| WO | 2016064795 | A4 | 4/2016 | |
| WO | 2016069788 | A1 | 5/2016 | |
| WO | 2016142392 | A1 | 9/2016 | |
| WO | 2018166533 | A1 | 9/2018 | |

OTHER PUBLICATIONS

McDuff, et al., "Remote Measurement of Cognitive Stress via Heart Rate Variability", 2014.
Yoo et al. (Jun. 17, 2011): Mental Stress Assessment Based on Pulse Photoplethysmography. IEEE 15' International Symposium on Consumer Electronics. pp. 323-326.
Bogdan et al. (May 2015): Remote Assessment of Heart Rate by Skin Color Processing. 2015 IEEE International Black Sea Conference on Communications and Networking. pp. I12-116.
Jimenez et al. "A practical appearance model for dynamic facial color", ACM Trans. Graph., 29(6):I41:I-141:I0, Dec. 2010.
Mohammed Hazim Alkawaz; The Correlation Between Blood Oxygenation Effects and Human Emotion Towards Facial Skin Colour of Virtual Human; Mar. 31, 2015; 3D Research Center, Kwangwoon University and Springer-Verlag.
Office Action for U.S. Appl. No. 16/076,522, United States Patent & Trademark Office, dated Jan. 31, 2020.
Notice of Allowance for U.S. Appl. No. 16/076,522, United States Patent & Trademark Office, dated Mar. 12, 2020.
Notice of Allowance for U.S. Appl. No. 16/875,339, United States Patent & Trademark Office, dated Aug. 26, 2020.
Office action for application 201780011835.9, The China National Intellectual Property Administration, dated Nov. 13, 2020.
International Search Report for PCT/CA2017/050207, Canadian Intellectual Property Office, dated May 31, 2017.
Written Opinion for PCT/CA2017/050207, Canadian Intellectual Property Office, dated May 31, 2017.
Antink et al. (Jul. 15, 2015): Beat-to-Beat Heart Rate Estimation Fusing Multimodal Video and Sensor Data. 2015 Optical Society of America. vol. 6 (8). pp. 2895-2907.

* cited by examiner

SYSTEM AND METHOD FOR DETECTING PHYSIOLOGICAL STATE

TECHNICAL FIELD

The following relates generally to health diagnostics and more specifically to an image-capture based system and method for detecting physiological state.

BACKGROUND

Tele-health service is the use of telecommunications and/or technology to provide healthcare-related services from a distance. It not only expands access to quality patient care, especially to rural regions and underserved populations, but also provides a way to cut down healthcare costs. It is changing the healthcare delivery model for the better. According to HIS, the number of patients using tele-health service will rise from roughly 350,000 in 2013 to at least 7 million by 2018.

The most common form of a tele-health service is a doctor consulting a patient via video-chat platform. However, if doctor want to gather more patient vital signs, such as heart rate, respiratory rate and blood pressure, various extra devices and training are required. These devices are invasive, generally expensive, and need to be purchased in advance of the consultation.

Early diagnosis of various conditions can improve the quality and length of life of many patients. One such condition is stress, which has become one of the leading health issues. Clinical researchers have found that stress is a major cause of a range of diseases from cardiovascular disease to depression to substance abuse. According to the American Institute of Stress, workplace stress costs United States more than 300 billion each year, not only in health care costs but also in missed work, employee turnover, worker compensation, and insurance.

Currently, there are mainly two approaches to measure a subject's stress level. The first approach relies on self-reporting. Researchers have developed a wide variety of questionnaires to determine the stress level of a patient. The second and more reliable and accurate approach is the measurement of physiological characteristics, such as blood pressure, vagal tone or salivary cortisol. All these measures require the use of advanced devices and professional training.

SUMMARY

In one aspect, a system for detecting physiological states from a captured image sequence of a subject, is provided the system comprising: a camera configured to capture an image sequence of the subject, the image sequence comprising a query set of images; a processing unit trained to determine a set of bitplanes of a plurality of images in the captured image sequence that represent hemoglobin concentration (HC) changes of the subject and that maximize signal differentiation between different physiological states; a classification machine, trained using a training set comprising HC changes of subjects with known physiological states, and configured to: detect the subject's physiological states based on HC changes in the set of bitplanes; and output the detected physiological states.

In another aspect, a method for detecting physiological states from a captured image sequence of a subject, is provided, the method comprising: capturing, by a camera, an image sequence of the subject, the image sequence comprising a query set of images; processing the captured image sequence, by a trained processing unit, to determine a set of bitplanes of a plurality of images in the captured image sequence that represent hemoglobin concentration (HC) changes of the subject and that maximize signal differentiation between different physiological states; processing the set of bitplanes, by a classification machine trained using a training set comprising HC changes of subjects with known physiological states, to: detect the subject's physiological states based on HC changes in the set of bitplanes; and output the detected physiological states.

BRIEF DESCRIPTION OF THE DRAWINGS

The features of the invention will become more apparent in the following detailed description in which reference is made to the appended drawings wherein.

DETAILED DESCRIPTION

Figure 1:
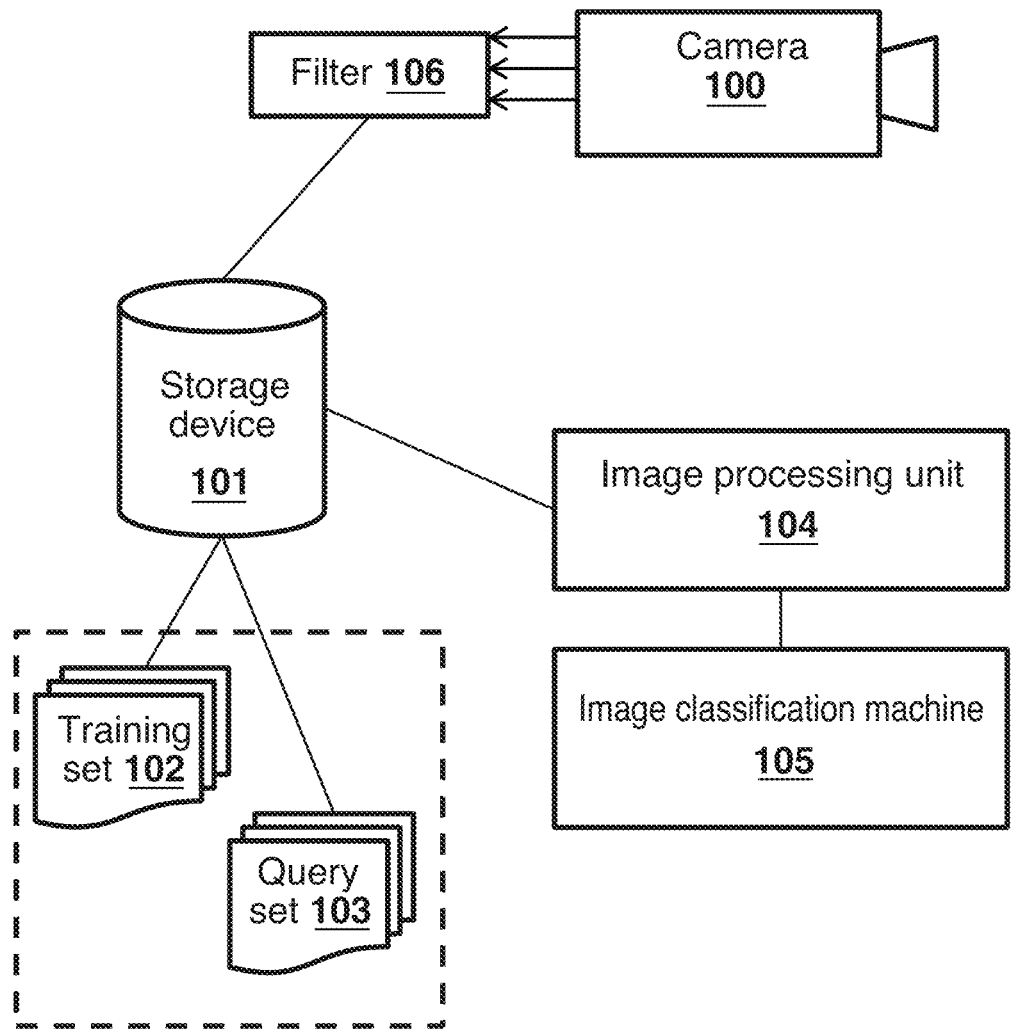
FIG. 1 is an block diagram of a transdermal optical imaging system for physiological state detection.

Embodiments will now be described with reference to the figures. For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Any module, unit, component, server, computer, terminal, engine or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

The following relates generally to the physiological diagnostics and more specifically to an image-capture based system and method for detecting health-related information, and specifically the physiological state of an individual captured in a series of images or a video. The system provides a remote and non-invasive approach by which to detect a physiological state with a high confidence. Many people have access to a digital camera and can thus obtain image sequences of themselves or others (such as family members) for purposes of analysis as disclosed herein. Such image sequences can be captured via, for example, a web cam, a smartphone forward or rear facing camera, a tablet camera, a conventional digital camera, etc. The image sequences can be transferred to a computing device for analysis via a computer network, removable media, etc.

The sympathetic and parasympathetic nervous systems are responsive to stress and pain. It has been found that an individual's blood flow is controlled by the sympathetic and parasympathetic nervous system, which is beyond the conscious control of the vast majority of individuals. Thus, an individual's internally experienced stress and pain can be readily detected by monitoring their blood flow. Internal stress and pain systems prepare humans to cope with different situations in the environment by adjusting the activations of the autonomic nervous system (ANS); the sympathetic and parasympathetic nervous systems play different roles in stress and pain regulation with the former up regulating fight-flight reactions whereas the latter serves to down regulating the stress reactions. Basic stress and pain states have distinct ANS signatures. Blood flow in most parts of the face such as eyelids, cheeks and chin is predominantly controlled by the sympathetic vasodilator neurons, whereas blood flowing in the nose and ears is mainly controlled by the sympathetic vasoconstrictor neurons; in contrast, the blood flow in the forehead region is innervated by both sympathetic and parasympathetic vasodilators. Thus, different internal physiological states have differential spatial and temporal activation patterns on the different parts of the face. By obtaining hemoglobin data from the system, facial hemoglobin concentration (HC) changes in various specific facial areas may be extracted. These multidimensional and dynamic arrays of data from an individual are then compared to computational models based on normative data to be discussed in more detail below. From such comparisons, reliable statistically based inferences about an individual's internal physiological states may be made. Because facial hemoglobin activities controlled by the ANS are not readily subject to conscious controls, such activities provide an excellent window into an individual's genuine innermost physiological state.

Figure 2:
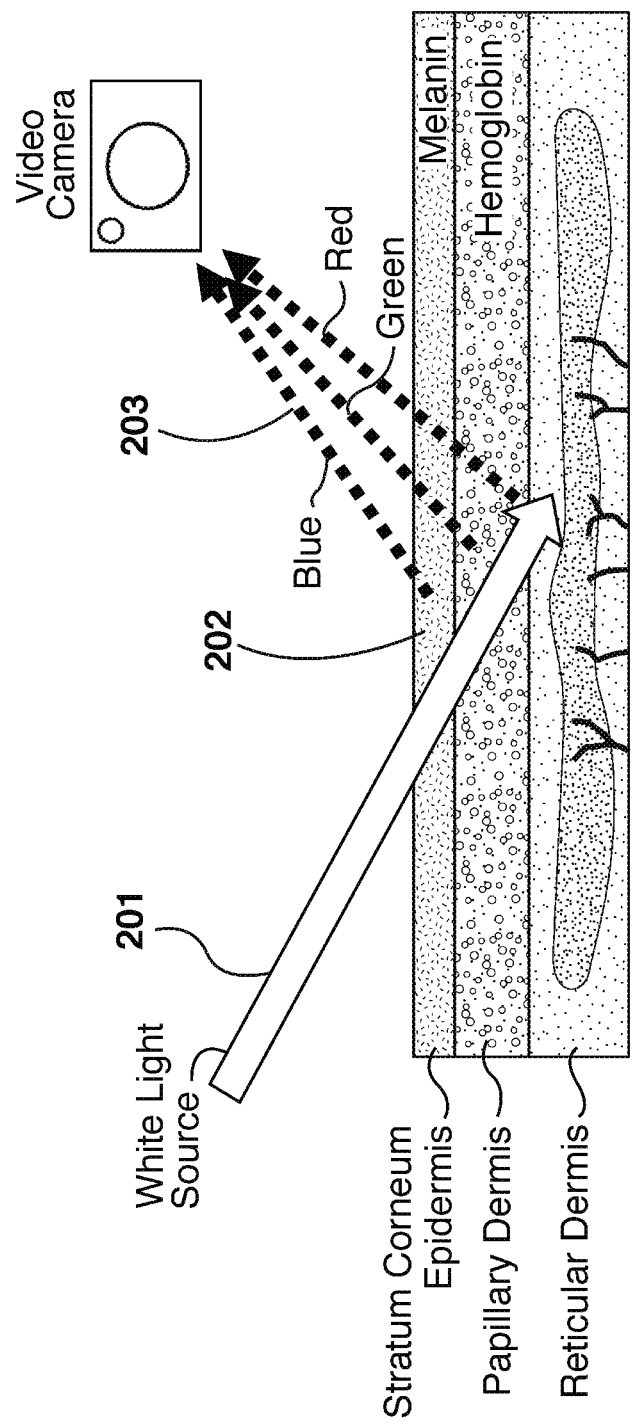
FIG. 2 illustrates re-emission of light from skin epidermal and subdermal layers.
Figure 3:
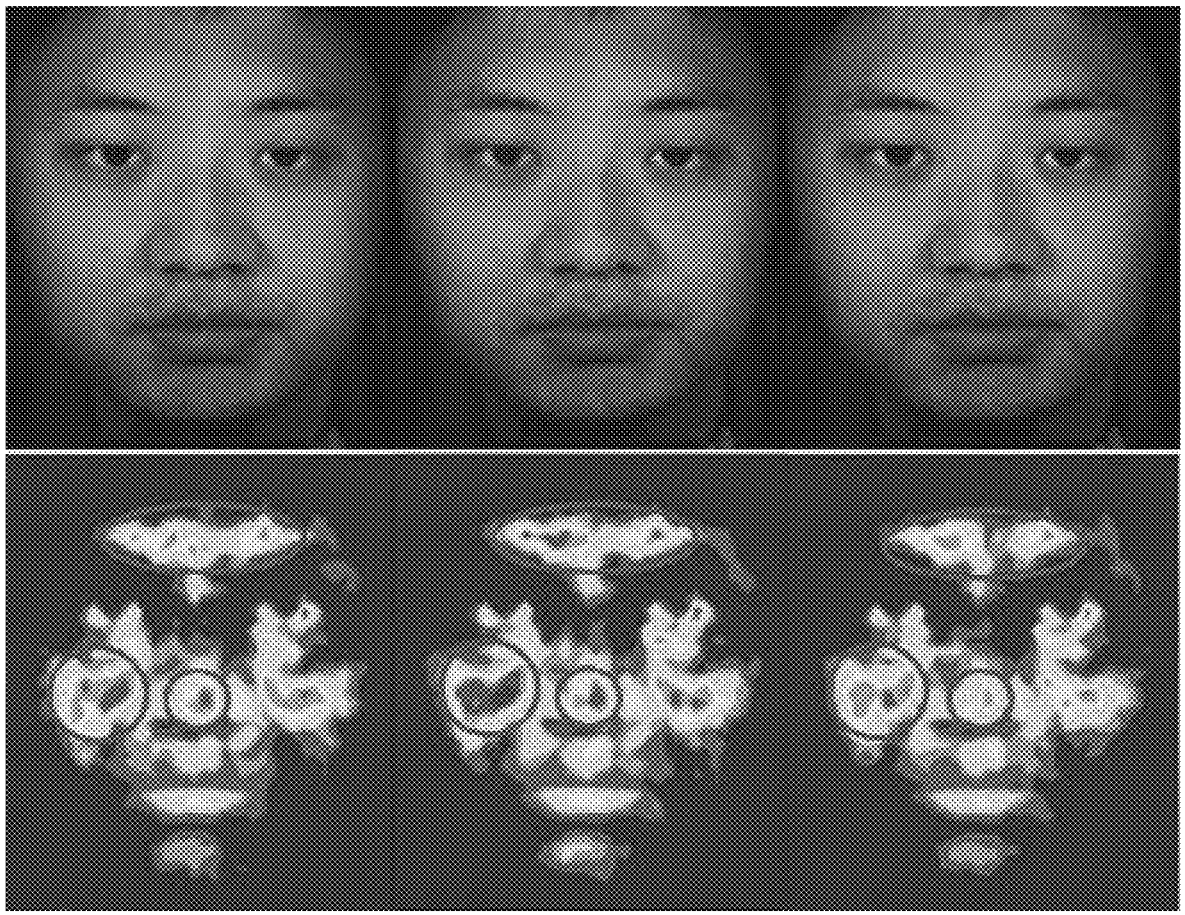
FIG. 3 is a set of surface and corresponding transdermal images illustrating change in hemoglobin concentration associated with a physiological state for a particular human subject at a particular point in time.

It has been found that it is possible to isolate hemoglobin concentration (HC) from raw images taken from a traditional digital camera, and to correlate spatial-temporal changes in HC to human physiological states. Referring now to FIG. 2, a diagram illustrating the re-emission of light from skin is shown. Light (201) travels beneath the skin (202), and re-emits (203) after travelling through different skin tissues. The re-emitted light (203) may then be captured by optical cameras. The dominant chromophores affecting the re-emitted light are melanin and hemoglobin. Since melanin and hemoglobin have different color signatures, it has been found that it is possible to obtain images mainly reflecting HC under the epidermis as shown in FIG. 3.

The system implements a two-step method to generate rules suitable to output an estimated statistical probability that a human subject's physiological state belongs to one of a plurality of physiological states, and a normalized intensity measure of such physiological state given a video sequence of any subject. The physiological states detectable by the system correspond to those for which the system is trained.

Referring now to FIG. 1, a system for physiological data detection in accordance with an embodiment is shown. The system comprises interconnected elements including an image processing unit (104), an image filter (106), and an image classification machine (105). The system may further comprise a camera (100) and a storage device (101), or may be communicatively linked to the storage device (101) which is preloaded and/or periodically loaded with video imaging data obtained from one or more cameras (100). The image classification machine (105) is trained using a training set of images (102) and is operable to perform classification for a query set of images (103) which are generated from images captured by the camera (100), processed by the image filter (106), and stored on the storage device (102).

Figure 7:
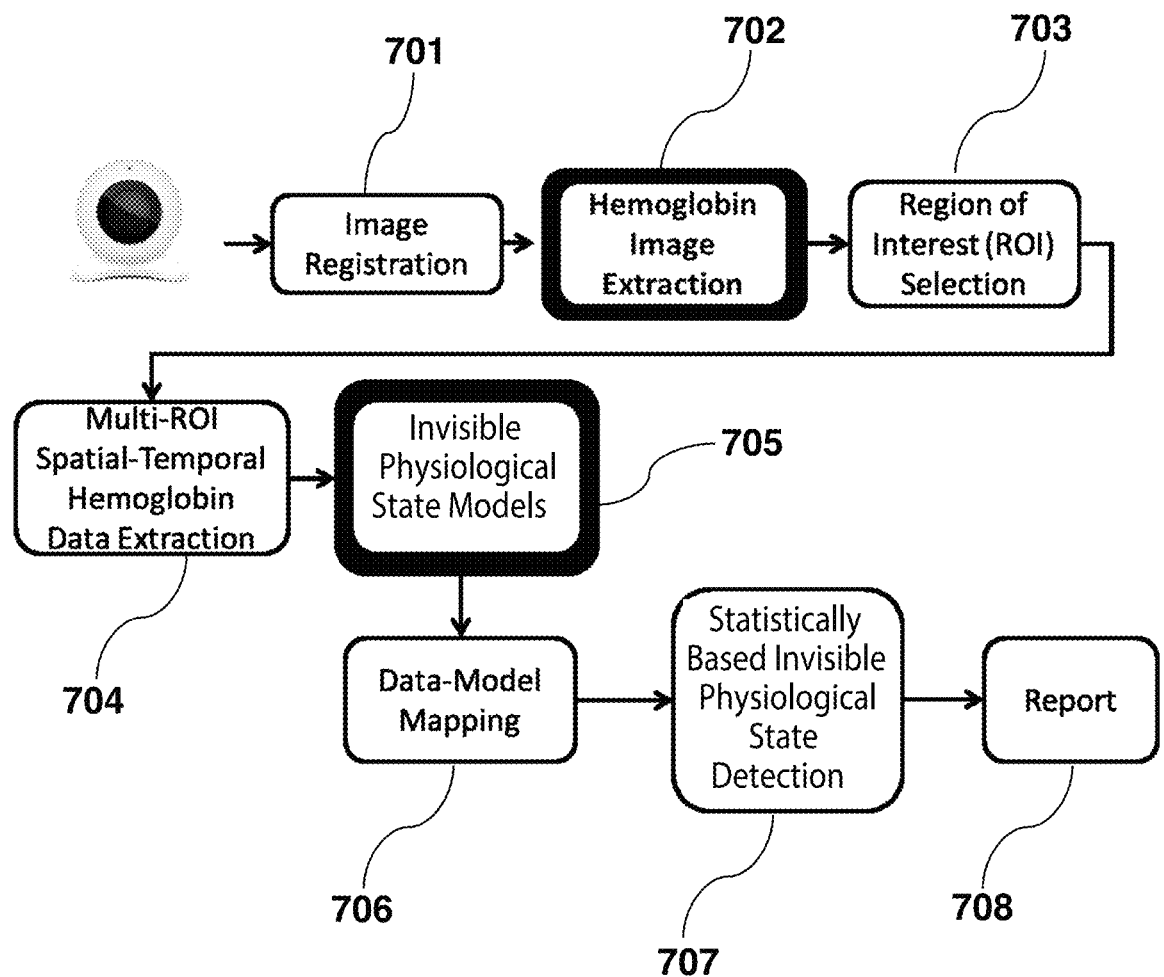
FIG. 7 is a flowchart illustrating a fully automated transdermal optical imaging and invisible physiological state detection system.
Figure 11:
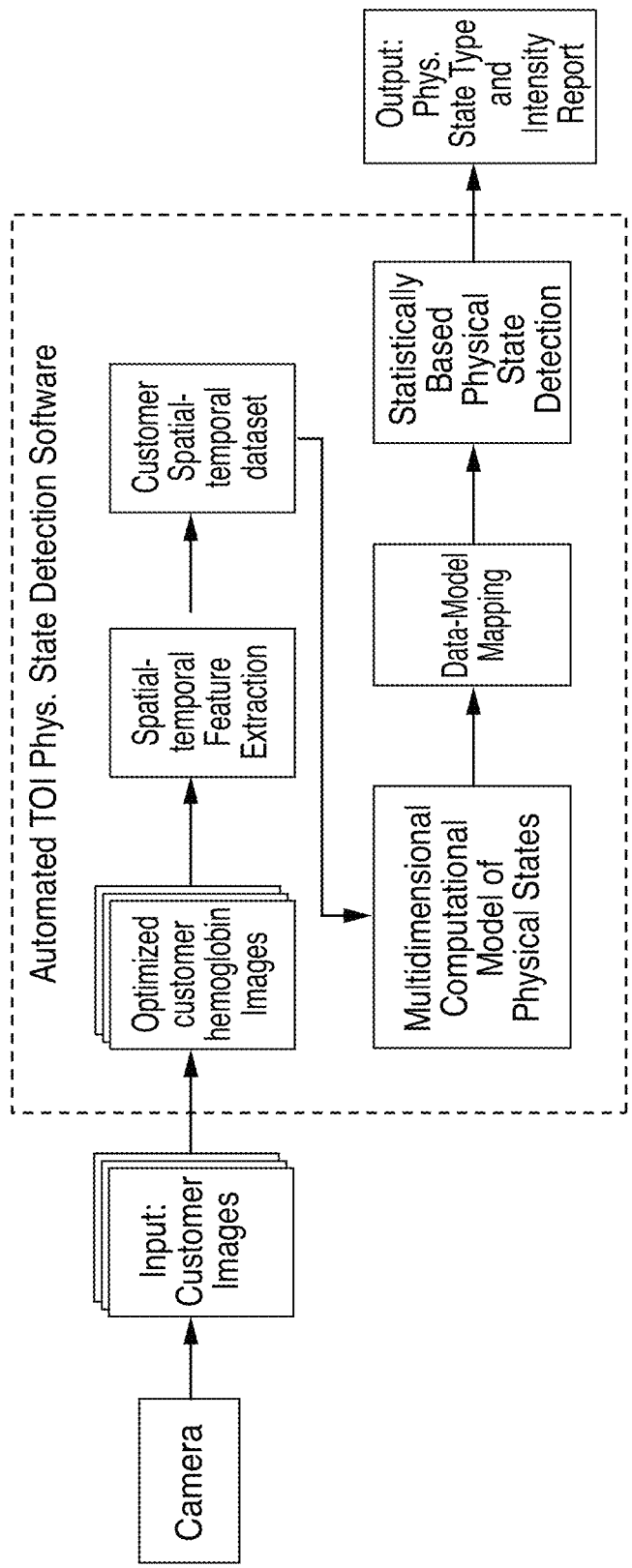
FIG. 11 is an illustration of an automated invisible physiological state detection system.

Referring now to FIG. 7, a flowchart illustrating a fully automated transdermal optical imaging and invisible physiological data detection system is shown. The system performs image registration 701 to register the input of a video sequence captured of a subject with an unknown physiological state, hemoglobin image extraction 702, ROI selection 703, multi-ROI spatial-temporal hemoglobin data extraction 704, invisible physiological state model 705 application, data mapping 706 for mapping the hemoglobin patterns of change, physiological state detection 707, and report generation 708. FIG. 11 depicts another such illustration of automated invisible physiological state detection system.

The image processing unit obtains each captured image or video stream and performs operations upon the image to generate a corresponding optimized HC image of the subject. The image processing unit isolates HC in the captured video sequence. In an exemplary embodiment, the images of the subject's faces are taken at 30 frames per second using a digital camera. It will be appreciated that this process may be performed with alternative digital cameras and lighting conditions.

Isolating HC is accomplished by analyzing bitplanes in the video sequence to determine and isolate a set of the bitplanes that provide high signal to noise ratio (SNR) and, therefore, optimize signal differentiation between different physiological states under the facial epidermis (or any part of the human epidermis). The determination of high SNR bitplanes is made with reference to a first training set of images constituting the captured video sequence, coupled with EKG, pneumatic respiration, blood pressure, laser Doppler, oximeter data from the human subjects from which the training set is obtained. The EKG, pneumatic respiration, blood pressure, and blood oxygenation data are firstly used to extract the heart rate, respiratory rate, blood pressure and blood oxygenation data from the HC data. The second step comprises training a machine to build a computational model for a particular physiological state using spatial-temporal signal patterns of transdermal HC changes in regions of interest ("ROIs") extracted from the optimized "bitplaned" images of a large sample of human subjects.

Heart rate, respiratory rate, blood pressure, blood oxygenation index Heart rate, respiratory rate, blood pressure and blood oxygenation data are obtained by analyzing bitplanes in the video sequence to determine and isolate a set of the bitplanes that are best correlated with the EKG, pneumatic respiration, blood pressure and the blood oxygenation machine data.

The human brain innervates the heart by means of stimuli via the autonomic nervous system (ANS, including sympathetic and parasympathetic nervous systems). The activation of sympathetic system leads to an increase of heart rate while the parasympathetic nervous system decreases the heart rate. As a result of a tug-of-war between these two systems, the heart modulates continually between acceleration and deceleration. The variance in time interval between heart beats (HRV) reflects the status of the autonomic nervous system.

More than a quarter-century of clinical research has shown that HRV can be a reliable indicator of a subject's stress level. When people are exposed to a stressor, the parasympathetic nervous system is suppressed and the sympathetic nervous system is activated. Hormones, such as epinephrine and norepinephrine, are secreted into the blood stream, leading to a series of physiological responses such as blood vessel constriction, blood pressure increase and heart rate variability decrease. When the stressor is no longer present, the body stops producing cortisol, the balance between sympathetic and parasympathetic system is re-established, and the heart rate variability increases again.

After an empirically-based HC isolation procedure, the set of bitplanes that provide the highest heart beat signal-to-noise ratio is determined, and the optimized heart beat signal is extracted. By defining the distance between two consecutive heart beat peaks, the heart beat interval time series data is calculated. Several digital signal transformations (e.g. Fourier transformations) are completed, and a stress level index is obtained. By comparing the stress level index against a normative stress index distribution profile that has been previously generated, a subject's comparative stress level can be assessed. A common heart-beat signal can be extracted from HC in any ROI, the system may utilize multiple ROIs to strengthen and improve this extracted the heart beat signal, because it is redundant information that is being carried in all/any ROI. Once determined, the stress level (and optionally heart beat signal) are available to be inputs to the classification machine for predicting the subject's overall physiological state. The stress index provides a valuable and distinct indication (separate from the heart beat signal from which it is actually derived, or from the HC changes) towards the prediction/classification of the subject physiological state.

For training, video images of test subjects exposed to stimuli known to elicit specific physiological states are captured. Responses may be grouped broadly (neutral, low, high) or more specifically (highly stressed, lowly stressed, highly pained, lowly pained, etc.). In further embodiments, levels within each physiological state may be captured. Preferably, subjects are instructed not to express their physiological state on the face so that the physiological reactions measured are invisible physiological states and expressed as changes in HC only. To ensure subjects do not "leak" physiological states in facial expressions, the surface image sequences may be analyzed with a facial physiological expression detection program. EKG, pneumatic respiratory, blood pressure, and laser Doppler, blood oxygenation data may further be collected using an EKG machine, a pneumatic respiration machine, a continuous blood pressure machine, a laser Doppler machine and oximeter and provides additional information to reduce noise from the bitplane analysis, as follows.

ROIs for physiological state detection (e.g., forehead, nose, and cheeks) are defined manually or automatically for the video images. These ROIs are preferably selected by subject matter experts who are steeped in the domain knowledge related to how HC is relevant as an indicator of physiological state. Using the native images that consist of all bitplanes of all three R, G, B channels, signals that change over a particular time period (e.g., 10 seconds) on each of the ROIs in a particular physiological state (e.g., stressed) are extracted. The process may be repeated with other physiological states (e.g., relaxed or neutral). The EKG and pneumatic respiration data may be used to prevent non-physiological state systemic HC signals from masking true physiological state-related HC signals. Fast Fourier transformation (FFT) may be used on the EKG, respiration, and blood pressure data to obtain the peek frequencies of EKG, respiration, blood pressure and blood oxygenation and then notch filers may be used to measure HC activities on the ROIs with temporal frequencies centering around these frequencies. Independent component analysis (ICA) may be used to accomplish the same goal.

Figure 9:
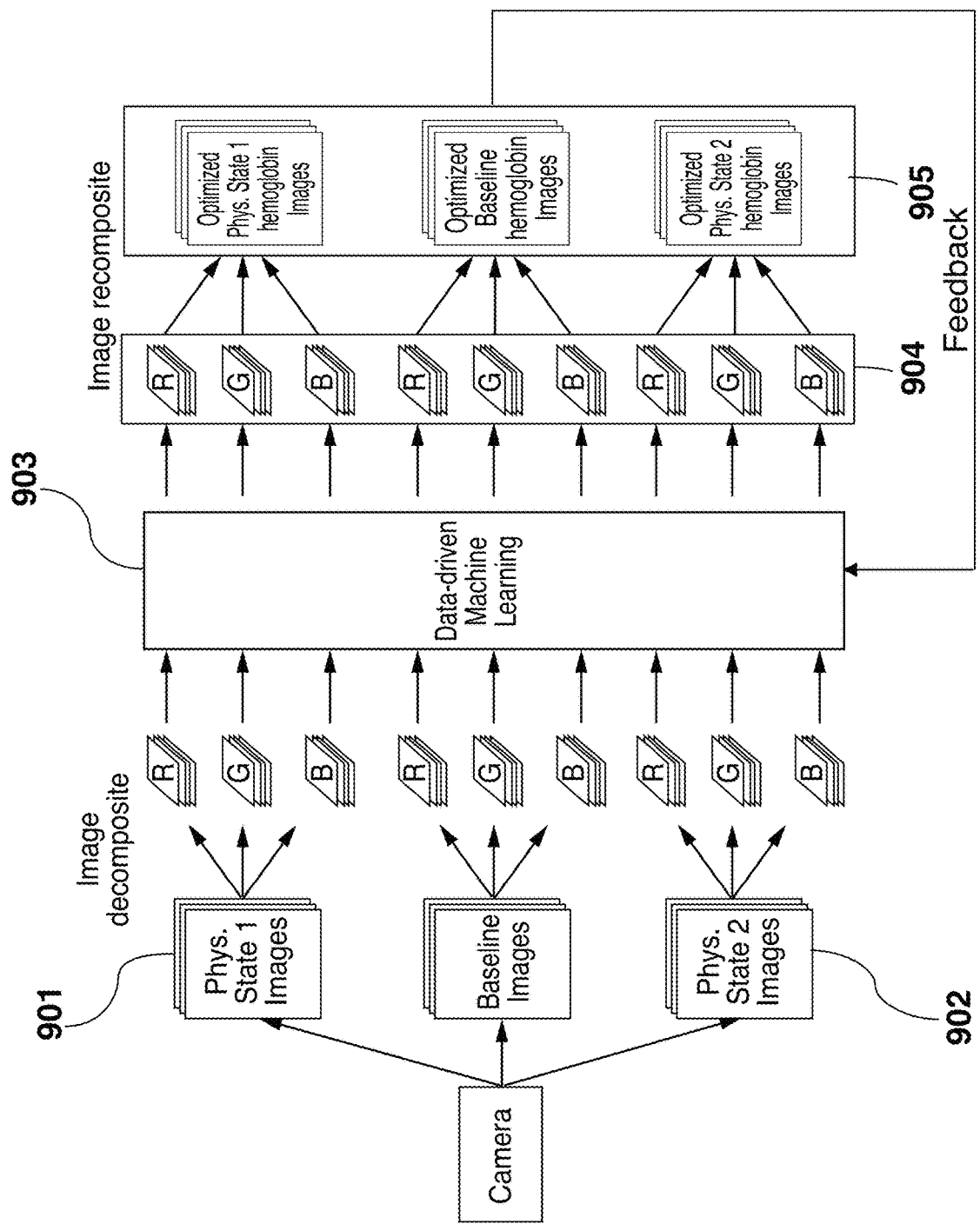
FIG. 9 is an illustration of a data-driven machine learning system for optimized hemoglobin image composition.

Referring now to FIG. 9 an illustration of data-driven machine learning for optimized hemoglobin image composition is shown. Using the filtered signals from the ROIs of two or more than two physiological states 901 and 902, machine learning 903 is employed to systematically identify bitplanes 904 that will significantly increase the signal differentiation between the different physiological state and bitplanes that will contribute nothing or decrease the signal differentiation between different physiological states. After discarding the latter, the remaining bitplane images 905 that optimally differentiate the physiological states of interest are obtained. More specifically, the bitplane selection comprises selecting the RGB pixel bit-combination which will maximize the signal-to-noise-ratio (SNR) of the signal differentiation between different physiological states. To further improve SNR, the result can be fed back to the machine learning 903 process repeatedly until the SNR reaches an optimal asymptote.

As determining the set of bitplanes that will maximize the SNR of the signal differentiation between different physiological states (e.g. maximizing for SNR of the heart beat signal) comprises a calibration, this determination may be conducted once during the extraction process or may be executed periodically, so as to continuously ensure the maximum SNR during the entirety of the extraction process. The frequency provides a trade off in the extraction time versus the desired quality of the signal.

The machine learning process involves manipulating the bitplane vectors (e.g., 11 8×8×8, 16×16×16) using image subtraction and addition to maximize the signal differences in all ROIs between different physiological states over the time period for a portion (e.g., 70%, 80%, 90%) of the subject data and validate on the remaining subject data. The addition or subtraction is performed in a pixel-wise manner. An existing machine learning algorithm, the Long Short Term Memory (LSTM) neural network, or a suitable alternative thereto is used to efficiently and obtain information about the improvement of differentiation between physiological states in terms of accuracy, which bitplane(s) contributes the best information, and which does not in terms of feature selection. The Long Short Term Memory (LSTM) neural network allows us to perform group feature selections and classifications. The LSTM machine learning algorithms are discussed in more detail below. From this process, the set of bitplanes to be isolated from image sequences to reflect temporal changes in HC is obtained. An image filter is configured to isolate the identified bitplanes in subsequent steps described below.

Figure 10:
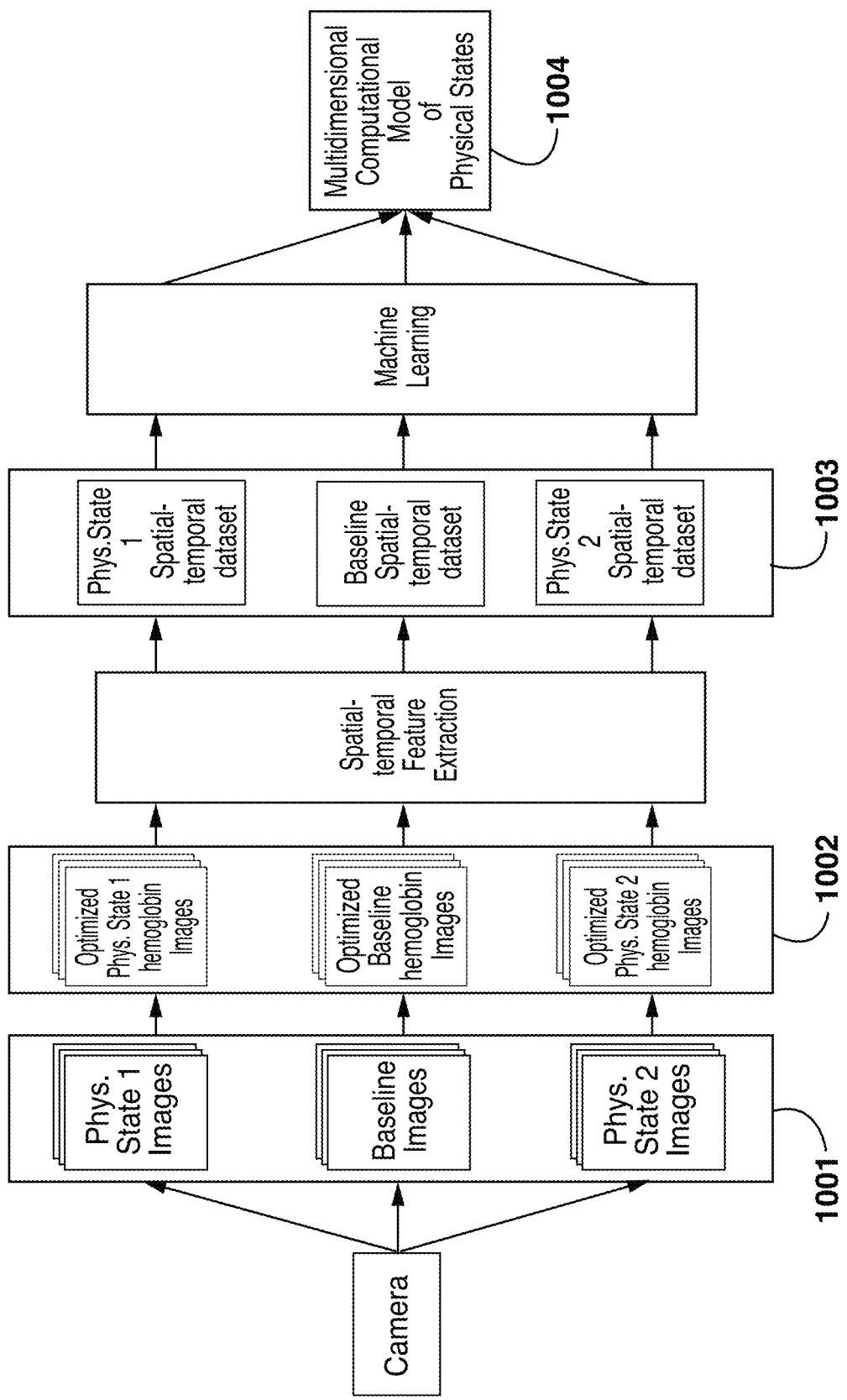
FIG. 10 is an illustration of a data-driven machine learning system for multidimensional physiological data model building.

The image classification machine 105, which has been previously trained with a training set of images captured using the above approach, classifies the captured image as corresponding to a physiological state. In the second step, using a new training set of subject physiological data derived from the optimized biplane images provided above, machine learning is employed again to build computational models for physiological states of interests (e.g., high vs. low risk for heart attack). Referring now to FIG. 10, an illustration of data-driven machine learning for multidimensional invisible physiological state model building is shown. To create such models, a second set of training subjects (preferably, a new multi-ethnic group of training subjects with different skin types) is recruited, and image sequences 1001 are obtained when they are exposed to stimuli eliciting known physiological response. An exemplary set of stimuli is the International Affective Picture System, which 1 has been commonly used to induce physiological dates and other well established physiological date-evoking paradigms. The image filter is applied to the image sequences 1001 to generate high HC SNR image sequences. The stimuli could further comprise non-visual aspects, such as auditory, taste, smell, touch or other sensory stimuli, or combinations thereof.

Using this new training set of subject physiological data 1003 derived from the bitplane filtered images 1002, machine learning is used again to build computational models for physiological states of interests (e.g., high vs. low risk for heart attack) 1003. Note that the physiological state of interest used to identify remaining bitplane filtered images that optimally differentiate the physiological states of interest and the state used to build computational models for physiological states of interests must be the same. For different physiological states of interests, the former must be repeated before the latter commences.

The machine learning process again involves a portion of the subject data (e.g., 70%, 80%, 90% of the subject data) and uses the remaining subject data to validate the model. This second machine learning process thus produces separate multidimensional (spatial and temporal) computational models of trained physiological states 1004.

To build different physiological models, facial HC change data on each pixel of each subject's face image is extracted (from Step 1) as a function of time when the subject is viewing a particular physiological date-evoking stimulus. To increase SNR, the subject's face is divided into a plurality of ROIs according to their differential underlying ANS regulatory mechanisms mentioned above, and the data in each ROI is averaged.

Figure 4:
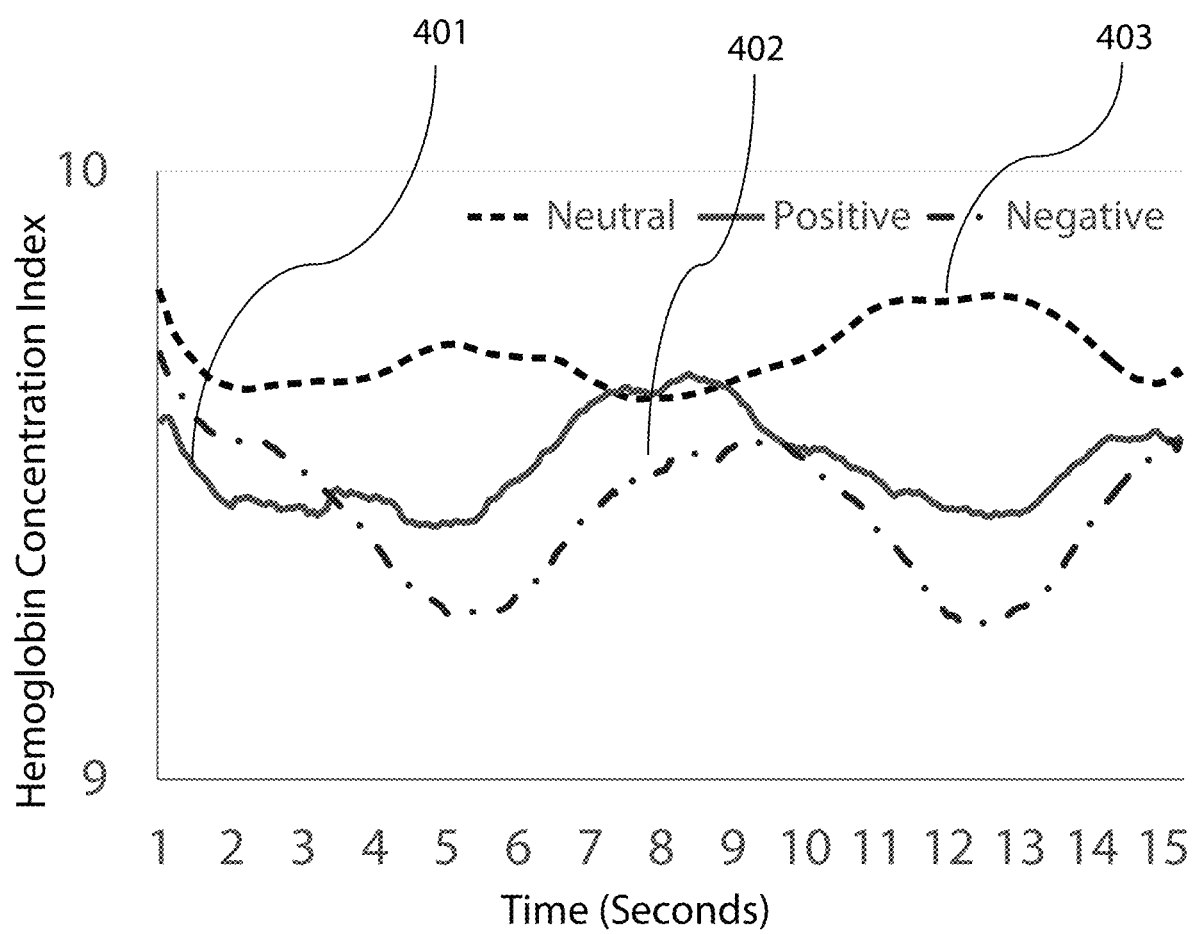
FIG. 4 is a plot illustrating hemoglobin concentration changes for the forehead of a subject who experiences positive, negative, and neutral physiological states as a function of time (seconds)
Figure 5:
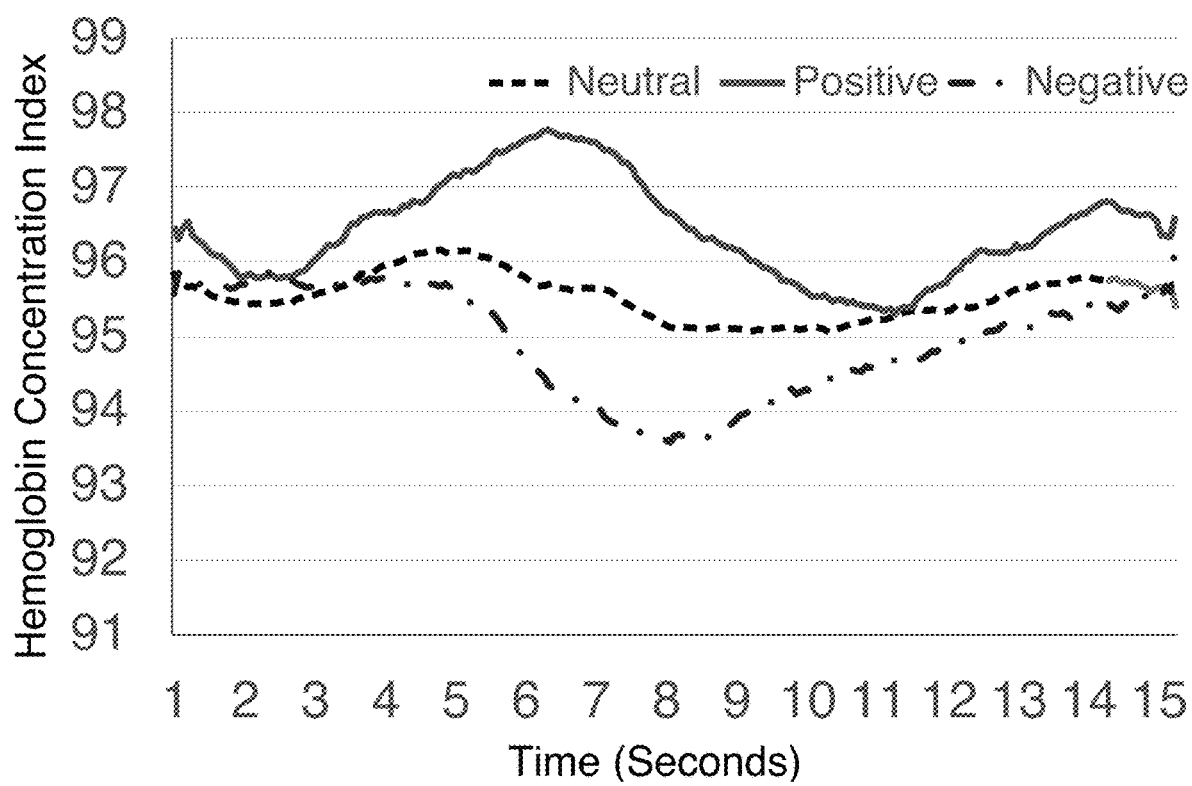
FIG. 5 is a plot illustrating hemoglobin concentration changes for the nose of a subject who experiences positive, negative, and neutral physiological states as a function of time (seconds)
Figure 6:
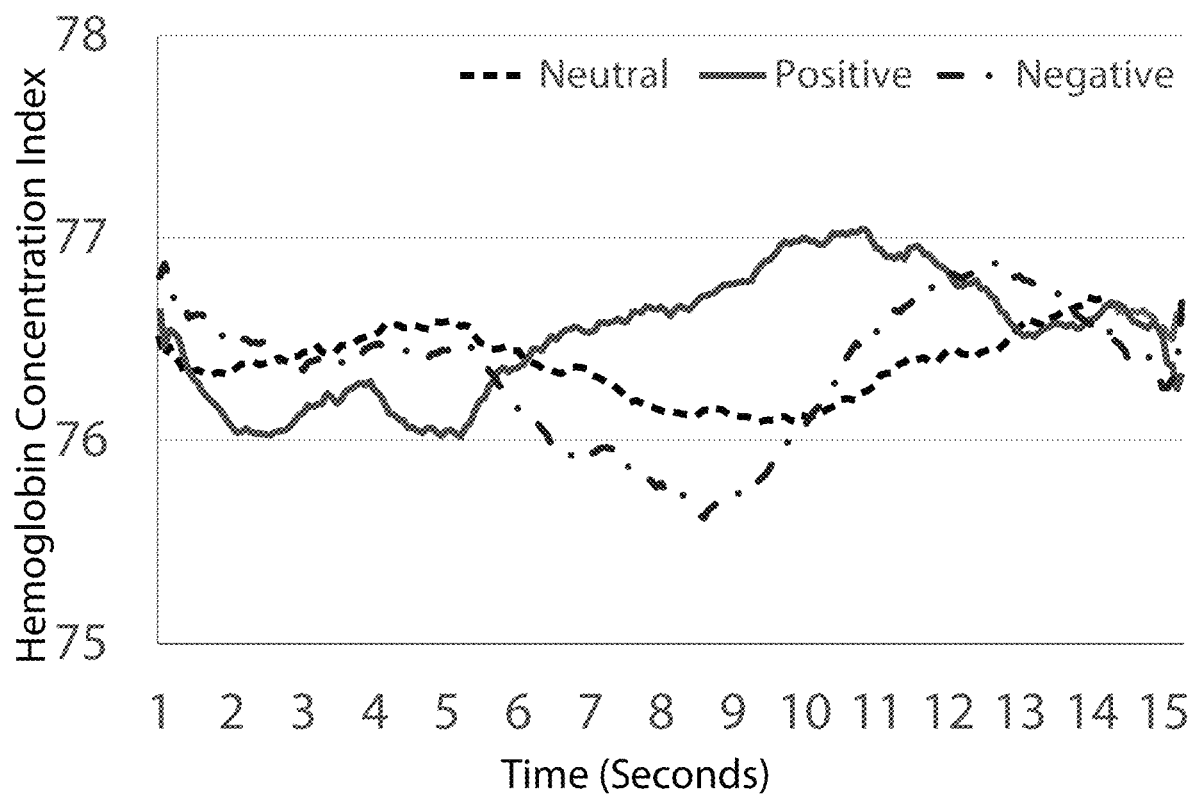
FIG. 6 is a plot illustrating hemoglobin concentration changes for the cheek of a subject who experiences positive, negative, and neutral physiological states as a function of time (seconds)

Referring now to FIG. 4, a plot illustrating differences in hemoglobin distribution for the forehead of a subject is shown. Though neither human nor computer-based facial expression detection system may detect any facial expression differences, transdermal images show a marked difference in hemoglobin distribution between positive 401, negative 402 and neutral 403 conditions. Differences in hemoglobin distribution for the nose and cheek of a subject may be seen in FIG. 5 and FIG. 6 respectively.

The Long Short Term Memory (LSTM) neural network, or a suitable alternative such as non-linear Support Vector Machine, and deep learning may again be used to assess the existence of common spatial-temporal patterns of hemoglobin changes across subjects. The Long Short Term Memory (LSTM) neural network machine or an alternative is trained on the transdermal data from a portion of the subjects 1 (e.g., 70%, 80%, 90%) to obtain a multidimensional computational model for each of the three invisible physiological categories. The models are then tested on the data from the remaining training subjects.

Following these steps, it is now possible to obtain a video sequence of any subject and apply the HC extracted from the selected biplanes to the computational models for physiological states of interest. The output will be (1) an estimated statistical probability that the subject's physiological state belongs to one of the trained physiological dates, and (2) a normalized intensity measure of such physiological state. For long running video streams when physiological states change and intensity fluctuates, changes of the probability estimation and intensity scores over time relying on HC data based on a moving time window (e.g., 10 seconds) may be reported. It will be appreciated that the confidence level of categorization may be less than 100%.

In further embodiments, optical sensors pointing, or directly attached to the skin of any body parts such as for example the wrist or forehead, in the form of a wrist watch, wrist band, hand band, clothing, footwear, glasses or steering wheel may be used. From these body areas, the system may also extract dynamic hemoglobin changes associated with physiological dates while removing heart beat artifacts and other artifacts such as motion and thermal interferences.

In still further embodiments, the system may be installed in robots and their variables (e.g., androids, humanoids) that interact with humans to enable the robots to detect hemoglobin changes on the face or other-body parts of humans whom the robots are interacting with. Thus, the robots equipped with transdermal optical imaging capacities read the humans' invisible physiological states and other hemoglobin change related activities to enhance machine-human interaction.

Two example implementations for (1) obtaining information about the improvement of differentiation between physiological states in terms of accuracy, (2) identifying which bitplane contributes the best information and which does not in terms of feature selection, and (3) assessing the existence of common spatial-temporal patterns of hemoglobin changes across subjects will now be described in more detail. One example of such implementation is a recurrent neural network.

Figure 12:
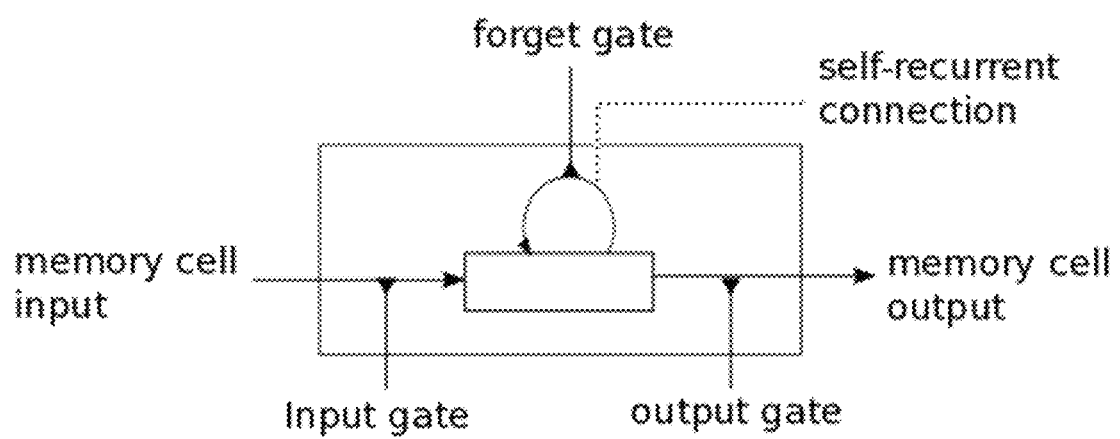
FIG. 12 is a memory cell.

One recurrent neural network is known as the Long Short Term Memory (LSTM) neural network, which is a category of neural network model specified for sequential data analysis and prediction. The LSTM neural network comprises at least three layers of cells. The first layer is an input layer, which accepts the input data. The second (and perhaps additional) layer is a hidden layer, which is composed of memory cells (see FIG. 12). The final layer is output layer, which generates the output value based on the hidden layer using Logistic Regression.

Each memory cell, as illustrated, comprises four main elements: an input gate, a neuron with a self-recurrent connection (a connection to itself), a forget gate and an output gate. The self-recurrent connection has a weight of 1.0 and ensures that, barring any outside interference, the state of a memory cell can remain constant from one time step to another. The gates serve to modulate the interactions between the memory cell itself and its environment. The input gate permits or prevents an incoming signal to alter the state of the memory cell. On the other hand, the output gate can permit or prevent the state of the memory cell to have an effect on other neurons. Finally, the forget gate can modulate the memory cell's self-recurrent connection, permitting the cell to remember or forget its previous state, as needed.

The equations below describe how a layer of memory cells is updated at every time step t. In these equations:

$x_t$ is the input array to the memory cell layer at time t. In our application, this is the blood flow signal at all ROIs $$\vec{x}_t = [x_{1t}, x_{2t}, \ldots, x_{nt}]$$

$W_i$, $W_f$, $W_c$, $W_o$, $U_i$, $U_f$, $U_c$, $U_o$ and $V_o$ are weight matrices; and $b_i$, $b_f$, $b_c$ and $b_o$ are bias vectors First, we compute the values for $i_t$, the input gate, and $\tilde{C}_t$ the candidate value for the states of the memory cells at time t:

$$i_t = \sigma(W_i x_t + U_i h_{t-1} + b_i)$$

$$\tilde{C}_t = \tanh(W_c x_t + U_c h_{t-1} + b_c)$$

Second, we compute the value for $f_t$, the activation of the memory cells' forget gates at time t:

$$f_t = \sigma(W_f x_t + U_f h_{t-1} + b_f)$$

Given the value of the input gate activation $i_t$, the forget gate activation $f_t$ and the candidate state value $\tilde{C}_t$, we can compute $C_t$ the memory cells' new state at time t:

$$C_t = i_t * \tilde{C}_t + f_t * C_{t-1}$$

With the new state of the memory cells, we can compute the value of their output gates and, subsequently, their outputs:

$$o_t = \sigma(W_o x_t + U_o h_{t-1} + V_o C_t + b_o)$$

$$h_t = o_t * \tanh(C_t)$$

Based on the model of memory cells, for the blood flow distribution at each time step, we can calculate the output from memory cells. Thus, from an input sequence $x_0$, $x_1$, $x_2$, ..., $x_n$, the memory cells in the LSTM layer will produce a representation sequence $h_0$, $h_1$, $h_2$, ..., $h_n$.

The goal is to classify the sequence into different conditions. The Logistic Regression output layer generates the probability of each condition based on the representation sequence from the LSTM hidden layer. The vector of the probabilities at time step t can be calculated by:

$$p_t = \text{softmax}(W_{output} h_t + b_{output})$$

where $W_{output}$ the weight matrix from the hidden layer to the output layer, and $b_{output}$ is the bias vector of the output layer. The condition with the maximum accumulated probability will be the predicted condition of this sequence.

Other machine training approaches such as deep learning may be used as well.

Figure 8:
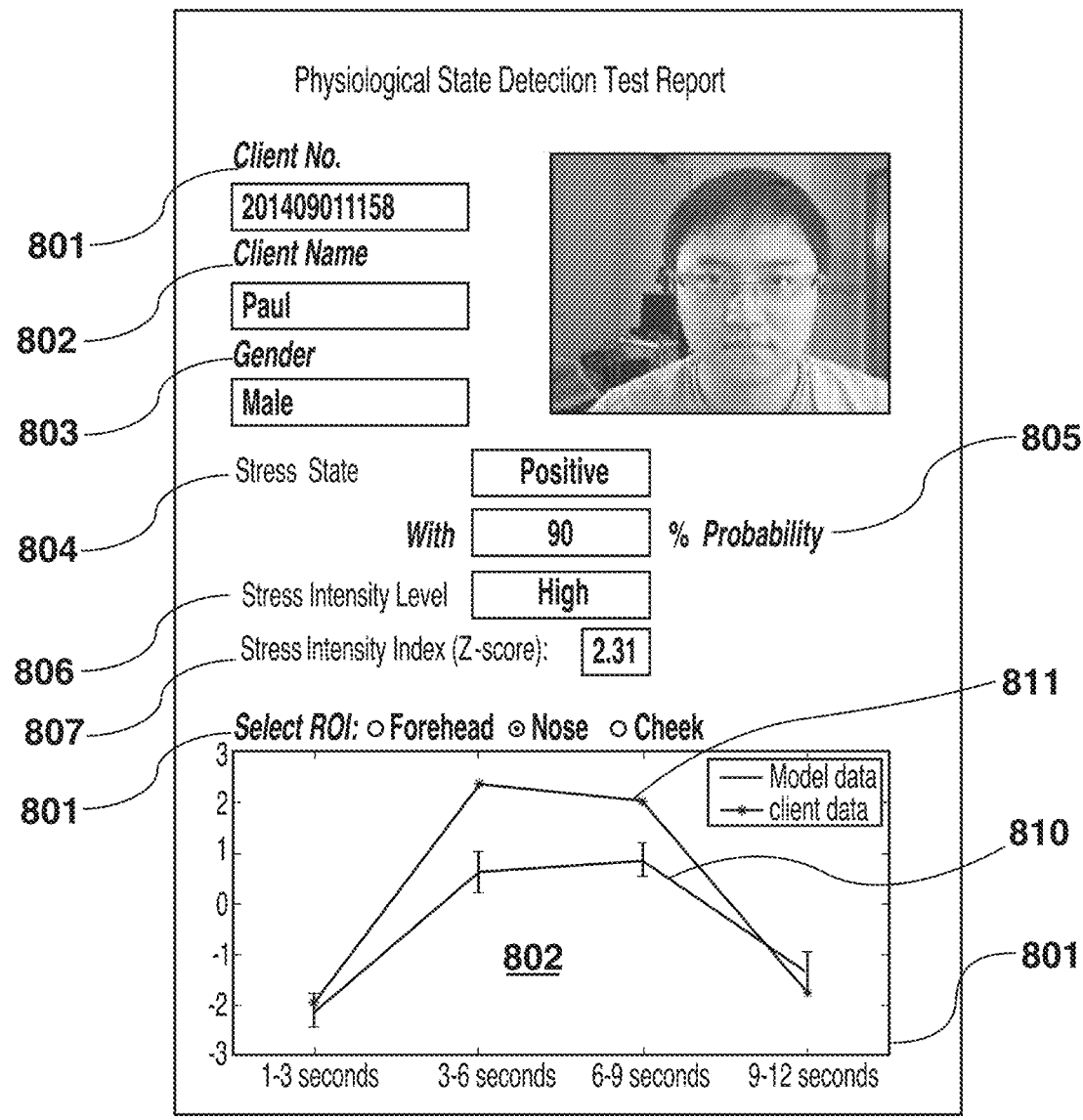
FIG. 8 is an exemplary report produced by the system.

Referring now to FIG. 8, an exemplary report illustrating the output of the system for detecting human physiological state is shown. The system may attribute a unique client number 801 to a given subject's first name 802 and gender 803. A physiological state 804 is identified with a given probability 805. The physiological state intensity level 806 is identified, as well as a physiological state intensity index score 807. In an embodiment, the report may include a graph comparing the physiological state shown as being felt by the subject 808 based on a given ROI 809 as compared to model data 810, over time 811.

While the above-described embodiment is directed to detecting stress, those skilled in the art will appreciate that the same approach can be used for detecting other physiological states. For example, this approach can be used to detect the presence or absence of pain in a subject. Since a pain state and a no pain state mainly activate the sympathetic and parasympathetic systems respectively, it is possible to differentiate between them by analyzing the spatial and temporal HC changes in the face of a subject. The best bitplanes set is determined for pain/no pain differentiation, a pain/no pain computational model is built using a machine learning method and this model is used to estimate the statistical probability that a subject is or is not experiencing pain.

The foregoing system and method may be applied to a plurality of fields, including personal physiological data capture. In one embodiment, a person can capture one or more sets of images of themselves using a conventional digital camera, such as a web camera, a camera built into a smartphone, etc. The sets of images can then be analyzed using a computing device that has the physiological data model built from training. This can be done locally, or remotely by transmitting the captured sets of images to another computing device, such as during a video-based tele-health session.

This approach can also be used to detect skin lesions that would normally be difficult to spot visually. Many kinds of skin lesions, from acne and pimples, to basal cell carcinoma and squamous-cell carcinoma, can lead to regional hemoglobin/melanin concentration abnormality and can be detected from transdermal structure images at a very early stage.

Further, some illnesses can be detected early via the above approach. This can be used to perform screening at borders and other checkpoints for communicable conditions.

In embodiments, the system may be used to determine the stress or pain state of a subject that is unable to speak and/or has muscular disabilities.

In other embodiments, the system can be used to quantify a subject's stress level during a stressful event to determine how well suited the particular subject is for a certain position, role, etc.

The system may be used to identify stress, pain, and fatigue levels felt by employees in a transport or military setting. For example, a fatigued driver, pilot, captain, soldier, etc., may be identified as too fatigued to effectively continue with shiftwork. In addition to safety improvements that may be enacted by the transport industries, analytics informing scheduling may be derived.

In yet another aspect, the system may be used by financial institutions looking to reduce risk with respect to trading practices or lending. The system may provide insight into the stress levels felt by traders, providing checks and balances for risky trading.

The system may be used by telemarketers attempting to assess user reactions to specific words, phrases, sales tactics, etc. that may inform the best sales method to inspire brand loyalty or complete a sale.

In still further embodiments, the system may be used as a tool in affective neuroscience. For example, the system may be coupled with a MRI or NIRS or EEG system to measure not only the neural activities associated with subjects' stress and/or pain but also the transdermal blood flow changes. Collected blood flow data may be used either to provide additional and validating information about subjects' stress and/or pain state or to separate physiological signals generated by the cortical central nervous system and those generated by the autonomic nervous system. For example, the blush and brain problem in fNIRS (functional near infrared spectroscopy) research where the cortical hemoglobin changes are often mixed with the scalp hemoglobin changes may be solved.

In still further embodiments, the system may detect physiological conditions that are elicited by sound in addition to vision, such as music, crying, etc. Physiological conditions that are elicited by other senses including smell, scent, taste as well as vestibular sensations may also be detected.

Other applications may become apparent.

Although the invention has been described with reference to certain specific embodiments, various modifications thereof will be apparent to those skilled in the art without departing from the spirit and scope of the invention as outlined in the claims appended hereto. The entire disclosures of all references recited above are incorporated herein by reference.

The invention claimed is:

1. A system for detecting physiological states from a captured image sequence of a human subject, the system comprising:
a processing unit trained to determine a set of bitplanes from the captured image sequence of the human subject that maximize signal-to-noise differentiation between different physiological states;
a trained image classification machine configured to:
detect the subject's physiological states using the set of bitplanes determined by the processing unit, the detection comprising calculating an estimated statistical probability that the subject's physiological state conforms to a known physiological state from training of the image classification machine, and a normalized intensity measure of such determined physiological state; and
output the detected physiological states.

2. The system of claim 1, wherein determining the set of bitplanes that maximize differentiation between different physiological states comprises selecting pixels that maximizes a heart beat signal-to-noise ratio.

3. The system of claim 1, wherein the set of bitplanes determined by the processing unit represent hemoglobin concentration (HC) changes and are determined for a selected plurality of regions of interest (ROI) of the subject that are relevant as an indicator of physiological state.

4. The system of claim 1, wherein outputting the subject's physiological states comprises grouping each of the detected physiological states into one of a plurality of groupings based on the calculated statistical probability and normalized intensity measure.

5. The system of claim 4, wherein the physiological states comprise stress levels, pain levels or fatigue levels.

6. The system of claim 1, further comprising one of a magnetic resonance imaging unit, a near-infrared spectroscopy imaging unit or an electroencephalography imaging unit for capturing a second image sequence of the human subject, and the processing unit is further configured to determine the subject's transdermal blood flow changes from the second image sequence of the human subject.

7. A method for detecting physiological states from a captured image sequence of a human subject, the method comprising:
processing the captured image sequence of the human subject, by a trained processing unit, to determine a set of bitplanes from the captured image sequence of the human subject that maximize signal-to-noise differentiation between different physiological states;
processing the set of bitplanes, by a trained classification machine to:
detect the subject's physiological states using the set of bitplanes determined by the processing unit, the detection comprising calculating an estimated statistical probability that the subject's physiological state conforms to a known physiological state from training of the image classification machine, and a normalized intensity measure of such determined physiological state; and
output the detected physiological states.

8. The method of claim 7, wherein determining the set of bitplanes that maximize differentiation between different physiological states comprises selecting pixels that maximizes a heart beat signal-to-noise ratio.

9. The method of claim 7, wherein the set of bitplanes determined by the processing unit represent hemoglobin concentration (HC) changes and are determined for a selected plurality of regions of interest (ROI) of the subject that are relevant as an indicator of physiological state.

10. The method of claim 7, wherein outputting the subject's physiological states comprises grouping each of the detected physiological states into one of a plurality of groupings based on the calculated statistical probability and normalized intensity measure.

11. The method of claim 10, wherein the physiological states comprise stress levels, pain levels or fatigue levels.

12. The method of claim 7, further comprising capturing a second image sequence of the human subject, by one of a magnetic resonance imaging unit, a near-infrared spectroscopy imaging unit or an electroencephalography imaging unit, and processing the second image sequence of the human subject to determine the subject's transdermal blood flow changes from the second image sequence of the human subject.

13. The system of claim 2, wherein the pixels that maximize the heart beat signal-to-noise ratio is determined by a machine learning model trained with a training set of images from the captured video sequence of the human subject and coupled with at least one of EKG, pneumatic respiration, blood pressure, laser Doppler, and oximeter data from the human subjects in the captured video sequence of the human subject.

14. The system of claim 13, wherein the detected physiological states comprise a risk for heart attack.

15. The method of claim 8, wherein the pixels that maximize the heart beat signal-to-noise ratio is determined by a machine learning model trained with a training set of images from the captured video sequence of the human subject and coupled with at least one of EKG, pneumatic respiration, blood pressure, laser Doppler, and oximeter data from the human subjects in the captured video sequence of the human subject.

16. The method of claim 15, wherein the detected physiological states comprise a risk for heart attack.

* * * * *